United States Patent [19]

Smitka et al.

[11] 4,436,750

[45] Mar. 13, 1984

[54] 12'-HYDROXYVERRUCARIN J AND ISO-SATRATOXIN H

[75] Inventors: Tim A. Smitka; Richard H. Bunge; James C. French, all of Ann Arbor; Russell J. Bloem, Dearborn, all of Mich.

[73] Assignee: Warner-Lambert Company, Morris Plains, N.J.

[21] Appl. No.: 432,467

[22] Filed: Oct. 4, 1982

[51] Int. Cl.[3] .................. C07D 493/22; A61K 31/365

[52] U.S. Cl. .................................... 424/279; 549/264

[58] Field of Search ......................... 549/264; 424/279

[56] References Cited

PUBLICATIONS

Robert M. Eppley et al., J. Org. Chem., vol. 42, (1977), pp. 240–243.

*Primary Examiner*—Norma S. Milestone

*Attorney, Agent, or Firm*—Jerry F. Janssen

[57] ABSTRACT

The present invention relates to the novel trichothecenes, 12'-hydroxyverrucarin J and iso-satratoxin H, and a fermentation process for the production of said compounds.

The invention also relates to pharmaceutical compositions comprising said compounds and methods for using said compositions.

3 Claims, 10 Drawing Figures

12'-HYDROXYVERRUCARIN J AND ISO-SATRATOXIN H

BACKGROUND OF THE INVENTION

The novel compounds of the invention, 12'-hydroxyverrucarin J, as represented by the structure in FIG. 1 and iso-satratoxin H, as represented by the structure in FIG. 2, are members of the trichothecene family of antibiotics, a review of which can be found in "Progress in the Chemistry of Natural Products," 31:64–117 (1974), by C. Tamm. 12'-Hydroxyverrucarin J is a novel compound that can be readily distinguished from all other reported trichothecenes by, among other features, the presence of a signal in the proton nuclear magnetic resonance spectrum (pmr) in $CDCl_3$ at 0.64 parts per million (ppm) downfield from tetramethylsilane (TMS) standard and the absence of the characteristics methyl singlet at ~2.3 ppm in verrucarin J and other trichothecenes having a 2'-double bond. Iso-satratoxin H is a novel stereoisomer of satratoxin H. The latter compound was reported by R. M. Eppley, E. P. Mazzola, R. J. Highet, and W. J. Bailey, *J. Org. Chem.* 42:240 (1977). Iso-satratoxin H is clearly distinguished from satratoxin H by, among other features, the presence of a signal in the proton nuclear resonance spectrum in $CDCl_3$ at 4.22 ppm downfield from TMS. No stereoisomers of satratoxin H have been reported in the chemical literature nor has a patent on any such stereoisomer been found to exist. The above properties, in addition to other properties described hereinafter, clearly establish 12'-hydroxyverrucarin J and iso-satratoxin H as novel trichothecenes. These compounds exhibit antimicrobial and antitumor properties when tested by standard procedures.

SUMMARY OF THE INVENTION

The invention sought to be patented in its chemical compound aspect are the chemical compounds 12'-hydroxyverrucarin J and iso-satratoxin H which are described and characterized herein.

The invention sought to be patented in its chemical process aspect is a process for the production of the compounds, 12'-hydroxyverrucarin J and iso-satratoxin H, which comprises cultivating a strain of the organism *Myrothecium roridum* in a suitable medium until substantial quantities of the compounds are formed.

The invention sought to be patented in its pharmaceutical composition aspect is a composition which comprises 12'-hydroxyverrucarin J or iso-satratoxin H and mixtures thereof in combination with a pharmaceutically acceptable carrier.

The invention sought to be patented in a first pharmaceutical method aspect is a method for treating microbial injections in a mammal which method comprises administering an antimicrobially effective amount of the above defined pharmaceutical composition to said mammal.

The invention sought to be patented in a second pharmaceutical method aspect is a method for treating tumors in a mammal which method comprises administering an antitumor effective amount of the above defined pharmaceutical composition to said mammal.

DESCRIPTION OF THE PREFERRED EMBODIMENTS

Figure 1:
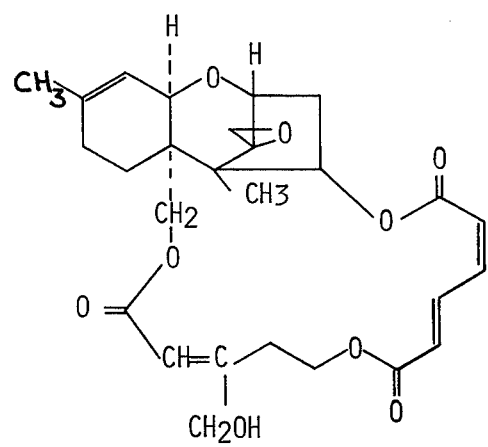
FIG. 1 is a representation of the structural formula of 12'-hydroxyverrucarin J.

The compounds of the invention, 12'-hydroxyverrucarin J and iso-satratoxin H may be produced by cultivating a selected 12'-hydroxyverrucarin J and iso-satratoxin H producing strain of an organism that closely resembles *Myrothecium roridum* Tode under artificial conditions in a suitable nutrient medium until substantial quantities of 12'-hydroxyverrucarin J and iso-satratoxin H are formed and isolating these compounds in pure form by procedures known in the art.

A new strain of a *Myrothecium roridum* species, suitable for the purpose of the invention, has been isolated from a sample of soil collected in Cleveland, Ohio. It corresponds morphologically to the description of this species by N. C. Preston, "Transactions Brit. Mycological Soc.," 26:158 (1943); and J. C. Gilman, "Manual of Soil Fungi," Second Edition 1957, The Iowa State College Press, Ames, Iowa. Cultures of this organism have been deposited with the U.S. Department of Agriculture, Northern Utilization Research and Development Division, Peoria, Ill., and are being maintained in their permanent culture collection as NRRL 12303.

The antitumor antibiotic compounds, 12'-hydroxyverrucarin J and iso-satratoxin H, are produced by the fungus during aerobic fermentation under controlled conditions. The fermentation medium consists of suitable sources of carbon, nitrogen, inorganic salts, and growth factors assimilable by the microorganism. Examples of carbon sources are various sugars such as cerelose, lactose, and maltose; starch, dextrin, corn meal, and glycerol. The normal quantity of the carbon sources varies from about 0.5 to 6% by weight, but levels outside of this range can also be used.

The sources of nitrogen can be of organic, inorganic, or mixed organic-inorganic in nature. Examples of the nitrogen sources that can be used in the culture medium are cottonseed meal, corn germ flour, soybean meal, corn steep liquor, distillers' solubles, peanut meal, fish meal, peptonized milk, and various ammonium salts. The normal amount added varies from 0.1 to 3% but higher amounts are also acceptable.

The inclusion of certain amounts of minerals and growth factors in the fermentation medium is also helpful in the production of 12'-hydroxyverrucarin J and iso-satratoxin H. Crude medium ingredients such as distillers' solubles, corn steep liquor, fish meal, yeast products, peptonized milk, and whey contain minerals and growth factors. However, inorganic salts such as potassium phosphate, sodium chloride, ferric sulfate, calcium carbonate, cobalt chloride, and zinc sulfate can be added to the fermentation medium.

The preferred method for producing 12'-hydroxyverrucarin J and iso-satratoxin H by *Myrothecium roridum* is by submerged fermentation. According to the embodiment of this invention, fermentation ingredients are prepared in solution and sterilized by autoclaving or steam heating. The pH of the aqueous medium is preferably between and six and eight. The fermentation medium is cooled to a suitable temperature, between 20°–45° C., and then inoculated with the suitable culture. Fermentation is carried out with aeration and agitation, and the maximum production of 12'-hydroxyverrucarin J and iso-satratoxin H is usually reached in about three to eight days.

In the submerged culture method, fermentation is carried out in shake flask or in stationary vat fermentors. In shake flasks, aeration is brought about by agitation of the flask which causes mixing of the medium with air. In the stationary fermentors, agitation is provided by impellers in the form of disc turbine, vaned disc, open turbine, or marine propeller; and aeration is accomplished by injecting air or oxygen into the fermentation mixture.

The examples which follow illustrate the preferred methods by which the products, 12'-hydroxyverrucarin J and iso-satratoxin H, of this invention are obtained. The described process is capable of wide variation, and any minor departure or extension is considered as within the scope of this invention.

Fermentation in 200-gallon Fermentors

A. Seed Development

A culture of the organism *Myrothecium roridum*, preserved in a soil tube, is transferred to CIM 23 agar slants and incubated at 28° C. for seven days.

| CIM-23 Slant Medium | |
| --- | --- |
| Amidex corn starch | 10 gm |
| N-Z Amine, Type A | 2 gm |
| Beef extract (Difco) | 1 gm |
| Yeast extract (Difco) | 1 gm |
| Cobalt chloride.6H$_2$O | 20 mg |
| Agar | 20 gm |
| Distilled water | 1,000 ml |

The microbial growths in two slants are scraped, suspended in distilled water, and used to inoculate a 30-liter seed fermentor. The seed fermentor is prepared by charging it with 16 liters of ARM 1558A medium and then autoclaving for 90 minutes at 121° C. and 15 pounds per square inch (psi) pressure.

| ARM 1558A Medium | |
| --- | --- |
| Cellulose | 2.0% |
| Pharmamedia | 0.3% |
| Defatted corn germ flour | 0.1% |
| Soybean meal | 0.1% |
| CaCO$_3$ | 1.0% |
| K$_2$SO$_4$.7H$_2$O | 0.1% |
| MgSO$_4$.7H$_2$O | 0.1% |
| NaCl | 0.05% |
| FeSO$_4$.7H$_2$O | 0.0001% |

Use tap water, no pH adjustment.

B. Production Fermentation

Two 200-gallon fermentation tanks are used for producing 12'-hydroxyverrucarin J and iso-satratoxin H. Each of these fermentors contains 160 gallons of pre-sterilized ARM 1558 medium.

| ARM 1558 Medium | |
| --- | --- |
| Cerelose | 5.0% |
| Pharmamedia | 0.3% |
| Defatted corn germ flour | 0.1% |
| Soybean meal | 0.1% |
| CaCO$_3$ | 1.0% |
| K$_2$HPO$_4$ | 0.1% |
| MgSO$_4$.7H$_2$O | 0.1% |
| NaCl | 0.05% |
| FeSO$_4$.7H$_2$O | 0.0001% |

Use tap water, no pH adjustment.

Each fermentor is inoculated with about 15 liters of the microbial growth from a 30-liter seed fermentor. The inoculated fermentors are stirred at 190 rpm at 30° C. and sparged with 20 cubic feet per minute (cfm) of air for 119 hours. An antifoam agent such as Dow Corning antifoam "C" is used to control foaming as required. Production of 12'-hydroxyverrucarin J and iso-satratoxin H in the fermentation broth is assayed versus KB and L1210 cell lines. An aliquot of the fermentation broth is mixed with growing cultures of KB and L1210 cells to give a final dilution of the fermentation broth of 1:100. Activity is expressed as the percent growth of the cells relative to the control (no fermentation broth added). A fermentation broth that gives percent growth values of 0–25% for KB and 0–50% for L1210 is considered active.

The activities of the fermentation broths after 119 hours of fermentation are:

| Inhibitory Zone (mm) | | Cytotoxicity (% growth) at a 1:100 dilution | |
| --- | --- | --- | --- |
| *Saccharomyces cerevisiae* | *Candida albicans* | L1210 | KB |
| 16 | 15 | 4 | 0 |
| 15 | 17 | 4 | 9 |

Isolation of 12'-hydroxyverrucarin J and iso-satratoxin H

The fermentation beers (a total of 1350 liters) from two 200-gallon fermentors prepared as described above are combined and mixed vigorously with 675 liters of ethyl acetate at pH 6.6 for one hour. Celite 45 (91 kg) is then added and the stirred mixture is filtered using a 75.8 cm plate and frame filter press. The filter cake is washed with 245 liters of ethyl acetate followed by 188 liters of deionized water. The filtrate and filter cake washes are combined and allowed to stand to permit the separation of phases. The upper organic phase amounts to about 660 liters; the lower aqueous phase (1520 liters) is separated and mixed with 340 liters of fresh ethyl acetate. After standing, the layers are separated and the upper organic layer (356 liters) is added to the first ethyl acetate extract. This combined ethyl acetate extract (1015 liters) is then concentrated in vacuo to 13.2 liters. The concentrated extract is dried using anhydrous sodium sulfate and then filtered. The solvent is removed in vacuo to leave approximately 900 g of an oily residue. This product, hereinafter referred to as residue A, is processed by the fractionation method described in the following example to afford pure samples of 12'-hydroxyverrucarin J and isosatratoxin H.

Purification Method

Figure 10:
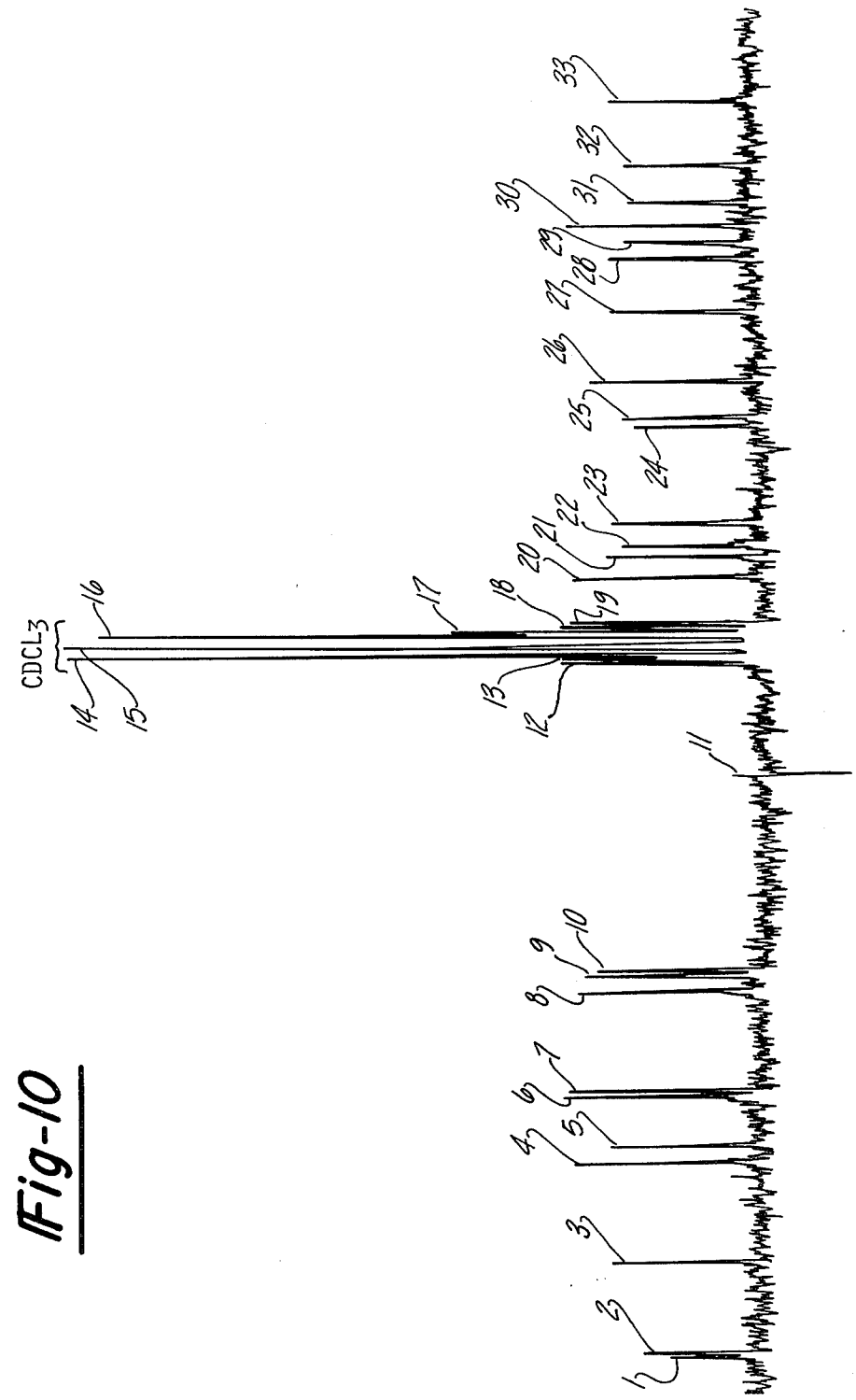
FIG. 10 is the carbon-13 nuclear magnetic resonance spectrum of iso-satratoxin H in deuterochloroform.

A solution of 118 g of Residue A in 2 liters of methylene chloride is fractionated using a Prep LC/System 500 apparatus fitted with two Prep Pak 500® silica gel cartridges (Waters Associates, Inc., Milford, Mass., USA). After application of the charge, the silica gel columns are eluted consecutively with 2.9 liters of methylene chloride; 4.3 liters of 75:25 methylene chloride:ethyl acetate; 6 liters of 50:50 methylene chloride:ethyl acetate; and 4 liters of ethyl acetate. Analysis of each fraction by means of high-performance liquid chromatography (HPLC) using a 0.39 cm (ID)×30 cm μ-Bondapak® (Waters Associates Inc., Mass., USA) $C_{18}$-silica gel column, a solvent system consisting of 65:35 methanol:water (v/v) and UV detection at 254 nm showed that the fractions representing the first 0.95 liters of the 75:25 methylene chloride:ethyl acetate (v/v) eluate contained the majority of 12'-hydroxyverrucarin J and iso-satratoxin H. These fractions were combined, dried over anhydrous sodium sulfate, and concentrated in vacuo to leave a residue (12 g). A portion (7.2 g) of this product dissolved in 50 ml methylene chloride is further fractionated by low pressure chromatography on 500 g of LPS-1 silica gel (Whatman, Inc., Clifton, N.J., USA) packed in a 4.8 cm (ID)×90 cm modified Michel-Miller column (Cat. Number 5820-875; Ace Glass Co., Vineland, N.J., USA). After the charge is applied, the silica gel is washed with one liter of hexane, and then eluted with a solvent system consisting of 80:20 hexane:n-propanol. The eluates are analyzed via HPLC on a 0.39 cm ID×30 cm silica gel μ Porasil® column using 80:20 hexane:n-propanol. (v/v) as the solvent. The fractions containing 12'-hydroxyverrucarin J are combined and concentrated to dryness in vacuo. The residue (1.37 g) is crystallized from methylene chloride-cyclohexane to yield 568 mg of 12'-hydroxyverrucarin J.

The fractions containing the iso-satratoxin H are concentrated to dryness and the residue (1.09 g), containing primarily iso-satratoxin H, was divided into four 270 mg aliquots. Each aliquot was chromatographed on 52 g of $C_{18}$-silanized silica gel (Analytichem International, Harbor City, Calif., USA) using a solvent system of acetonitrile/water (40/60, v/v). Those fractions found to contain primarily iso-satratoxin H by the HPLC system previously described were combined, concentrated in vacuo to remove the acetonitrile, and extracted three times with ethyl acetate. The ethyl acetate extracts were combined, dried over anhydrous sodium sulfate, and concentrated to dryness. The residue (229 mg) was rechromatographed over the $C_{18}$-column described previously, using a solvent system of 60:40 methanol/water (v/v). The fractions containing iso-satratoxin H were combined, concentrated, and dried in the same manner as before, yielding 200 mg of a residue which is crystallized from methylene chloride:cyclohexane to yield 139 mg of iso-satratoxin H.

Properties of 12'-hydroxyverrucarin J

White crystalline solid, mp >250° C.

Ultraviolet Absorption Spectrum in Methanol (FIG. 3).

| λmax | $a_1^1$ | ε |
|---|---|---|
| 217 nm | 470 | 23,500 |
| 262 nm | 377 | 18,900 |

Infrared Absorption Spectrum in $CCl_4$ (FIG. 4).

Principal absorptions at: 3640, 2980, 2920, 1745, 1660, 1270, 1210, and 1190 reciprocal centimeters.

Proton Nuclear Magnetic Resonance Spectrum in $CDCl_3$ (FIG. 5). Principal signals at: (s=singlet, d=doublet, t=triplet, dd=double doublet, dt=double triplet, m=multiplet).

0.64s; 1.25 s (cyclohexane); 1.72 s; 1.95 m; 2.05 m; 2.19 dt (J=6,17); 2.3 m; 2.45 dd (J=8,17); 2.83 d (J=4); 3.14 d (J=4); 3.66 d (J=5); 3.68 d (J=12); 3.86 d (J=6); 4.14 m; 4.20 d (J=16); 4.27 d (J=16); 4.97 m; 5.07 d (J=12); 5.30 s (methylene chloride); 5.44 dd (J=2,5); 5.90 d (J=16); 5.98 dd (J=4,8); 6.09 d (J=2); 6.10 d (J=11); 6.65 t (J=11); 7.27 s (chloroform); 8.20 dd (J=11,16) parts per million downfield from tetramethylsilane.

Carbon-13 Nuclear Magnetic Resonance Spectrum in $CDCl_3$ (FIG. 6). Principal signals at:

| | | | | |
|---|---|---|---|---|
| 166.08 | 116.72 | | 61.76 | |
| 165.86 | 79.18 | | 49.40 | |
| 165.27 | 78.48 | } $CDCl_3$ | 48.11 | |
| 157.39 | 77.02 | } $CDCl_3$ | 43.74 | |
| 141.32 | 75.62 | } $CDCl_3$ | 34.84 | |
| 139.97 | 75.13 | | 28.10 | |
| 139.38 | 67.64 | | 26.86 | |
| 127.30 | 65.21 | | 23.24 | |
| 124.98 | 64.40 | | 20.71 | |
| 118.29 | 62.73 | | 7.01 | Parts per million downfield from tetramethylsilane. |

| Elemental Analysis | % C | % H |
|---|---|---|
| Calcd for $C_{27}H_{32}O_9$ | 64.79 | 6.44 |
| Found | 65.20 | 6.55 |

Properties of iso-satratoxin H

White crystalline solid mp 168°-171° C. (uncorrected).

Ultraviolet Absorption Spectrum in Methanol (FIG. 7).

| λmax | $a_1^1$ | ε |
|---|---|---|
| 226 nm | 362 | 19,100 |
| 265 inflection | (219) | 11,600 |

Infrared Absorption Spectrum in $CCl_4$ (FIG. 8).

Principal absorption at: 3560, 3440, 2975, 2930, 2855, 1730, 1660, 1595, 1195, 1165, 1145, 1090, 1080, and 970 reciprocal centimeters.

Proton Nuclear Magnetic Resonance Spectrum in $CDCl_3$ (FIG. 9). Principal signals at: (s=singlet, t=triplet, q=quartet, m=multiplet, dd=double doublet, dt=double triplet).

0.83 s; 1.35 d (J=7); 1.43 s (cyclohexane); 1.61 s ($H_2O$); 1.72 s; 1.92 m; 2.18 dt (J=5,15); 2.45 dd (J=8,15); 2.78 m; 2.83 d (J=4); 3.14 d (J=4); 3.39 s; 3.59 d (J=5); 3.9 m; 4.22 s; 4.54 d (J=13); 5.06 s; 5.39 d (J=17); 5.43 d (J=5); 5.80 d (J=3); 5.9 m; 5.93 d (J=12); 6.52 dd (J=10,12); 7.26 dd (J=10,17); 7.27s (chloroform) parts per million downfield from tetramethylsilane.

Carbon-13 Nuclear Resonance Spectrum in CDCl₃ (FIG. 10). Principal signals at:

| | | | |
|---|---|---|---|
| 166.67 | 79.13 | | 61.05 |
| 166.35 | 78.69 | | 48.97 |
| 154.91 | 78.42 | ⎫ | 48.05 |
| 142.35 | 77.02 | ⎬ CDCl₃ | 43.36 |
| 140.40 | 75.62 | ⎭ | 34.46 |
| 134.15 | 75.35 | | 27.61 |
| 133.56 | 74.65 | | 25.45 |
| 120.98 | 74.16 | | 23.30 |
| 118.88 | 68.23 | | 20.33 |
| 118.23 | 65.48 | | 15.80 |
| 93.10* | 64.02 | | 7.54 Parts per million downfield from tetramethylsilane |

*Instrument noise

| Elemental Analysis | % C | % H |
|---|---|---|
| Calcd for C₂₉H₃₆O₉ | 65.91 | 6.81 |
| Found | 66.42 | 76.34 |

Mass Spectrum: Molecular ion at 528.

| High Performance Liquid Chromatography | |
|---|---|
| I. Column | μ Porasil (3.9 mm ID × 30 cm) |
| System | 90:10 hexane:propanol |
| Flowrate | 1.5 ml/minute |
| Dectection | ultraviolet absorption at 254 nm |
| Retention time | 8.3 minutes |
| II. Column | μ Bondapak (3.9 mm ID × 30 cm) |
| System | methanol:water 65.35 |
| Flowrate | 2 ml/minute |
| Retention time | 4.8 minutes |

Antimicrobial Activity of 12'-hydroxyverrucarin J and iso-satratoxin H.

Diameter of Inhibition Zone (12.7 mm disks)

| | 12'-hydroxy-verrucarin J | | iso-satratoxin H | |
|---|---|---|---|---|
| Organism | 0.5 mg/ml | 0.1 mg/ml | 0.5 mg/ml | 0.1 mg/ml |
| Endomycopsis fibuliger | 25.0 | 17.0 | 29.0 | 26.0 |
| Kloeckera africana | 22.5 | 0 | 20.0 | 0 |
| Kloeckera brevis | 14.0 | 0 | 18.0 | 0 |
| Pichia membranaefaciens | 13.5 | 0 | 0 | 0 |
| Rhodotorio glutinis | 29.0 | 20.5 | 25.0 | 20.0 |
| Saccharomyces cerevisiae | 20.0 | 13.5 | 17.0 | 0 |
| Saccharomyces fragilis | 30.0 | 27.0 | 29.0 | 25.0 |
| Saccharomyces italicus | 19.5 | 16.5 | 17.0 | 0 |
| Saccharomycoides ludwigii | 31.0 | 25.0 | 29.0 | 23.0 |

Both 12'-hydroxyverrucarin J and iso-satratoxin H inhibit more than 95% of the growth of L1210 cells in vitro at a concentration of 0.067 μg/ml.

The following zones of inhibition of KB cells and human colon adenocarcinoma in agar are produced when 6.5 mm paper disks are moistened with the specified solutions.

| | | Inhibitory Zone (mm) | |
|---|---|---|---|
| | | KB | HCA |
| 12'-hydroxy-verrucarin J | 100 μg/ml | 36 | 25 |
| | 33 μg/ml | 32 | 20 |
| | 10 μg/ml | 30 | 13 |
| iso-satratoxin H | 100 μg/ml | 44 | 21 |
| | 33 μg/ml | 44 | 17 |
| | 10 μg/ml | 40 | 12 |

Antitumor Activity of 12'hydroxyverrucarin J and iso-satratoxin H against P388 Lymphatic Leukemia in Mice

| | Dose | T/C percent MST* | |
|---|---|---|---|
| | (mg/kg) | test - 1 | test - 2 |
| 12'-hydroxy-verrucarin J (Q4D × 2) | 2.50 | 122 | 129 |
| | 1.25 | 125 | 129 |
| | 0.63 | — | 123 |
| | 0.31 | — | 116 |
| iso-satratoxin H (QD × 5) | 2.0 | 171 | 198 |
| | 1.0 | 152 | 177 |
| | 0.5 | 138 | 144 |
| | 0.25 | — | 125 |

*T/C percent MST = 100 × median survival time in days of treated/control mice. Values ≧ 125 are considered to show activity. The test method used is based on that described in Cancer Chemother. Reports 3: 1-87 (part 3), 1972.

Figure 2:
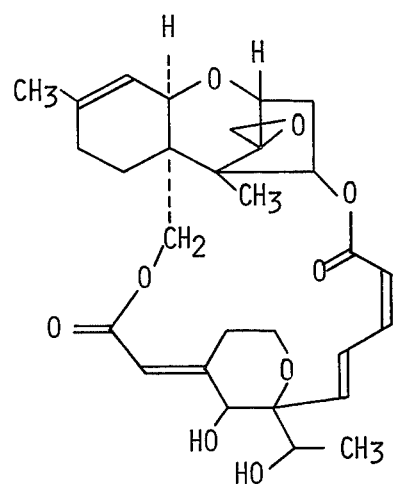
FIG. 2 is a representation of the structural formula of iso-satratoxin H.
Figure 3:
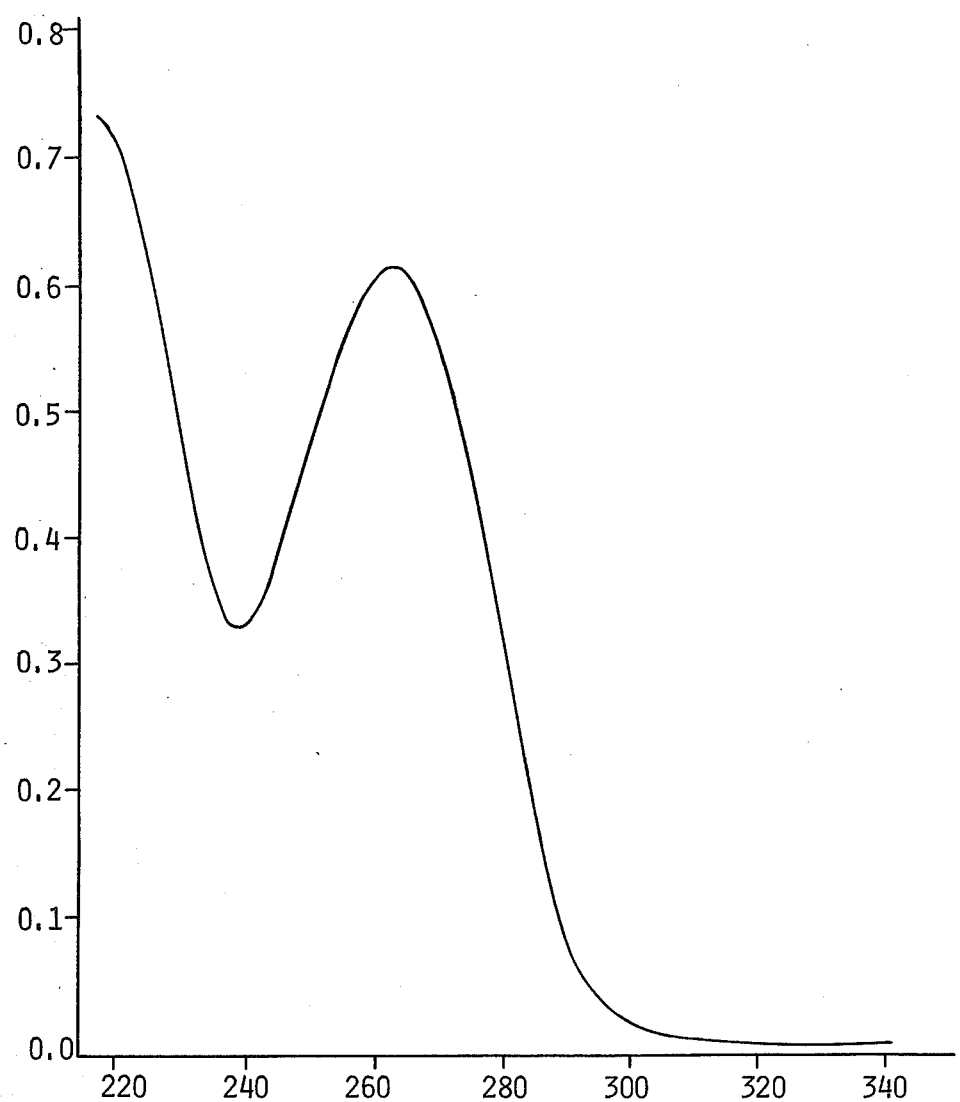
FIG. 3 is the ultraviolet absorption spectrum of 12'-hydroxyverrucarin J in methyl alcohol.
Figure 4:
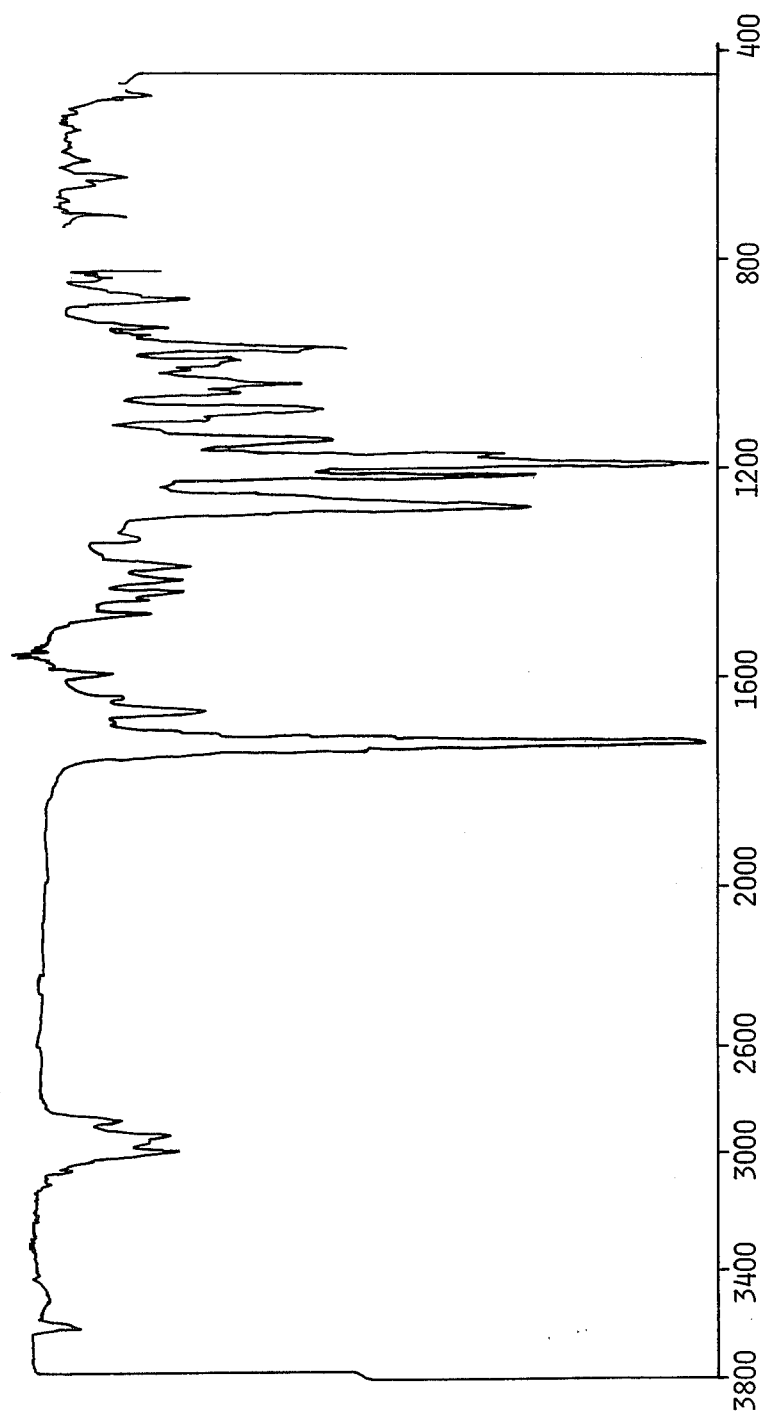
FIG. 4 is the infrared absorption spectrum of 12'-hydroxyverrucarin J in carbon tetrachloride.
Figure 5:
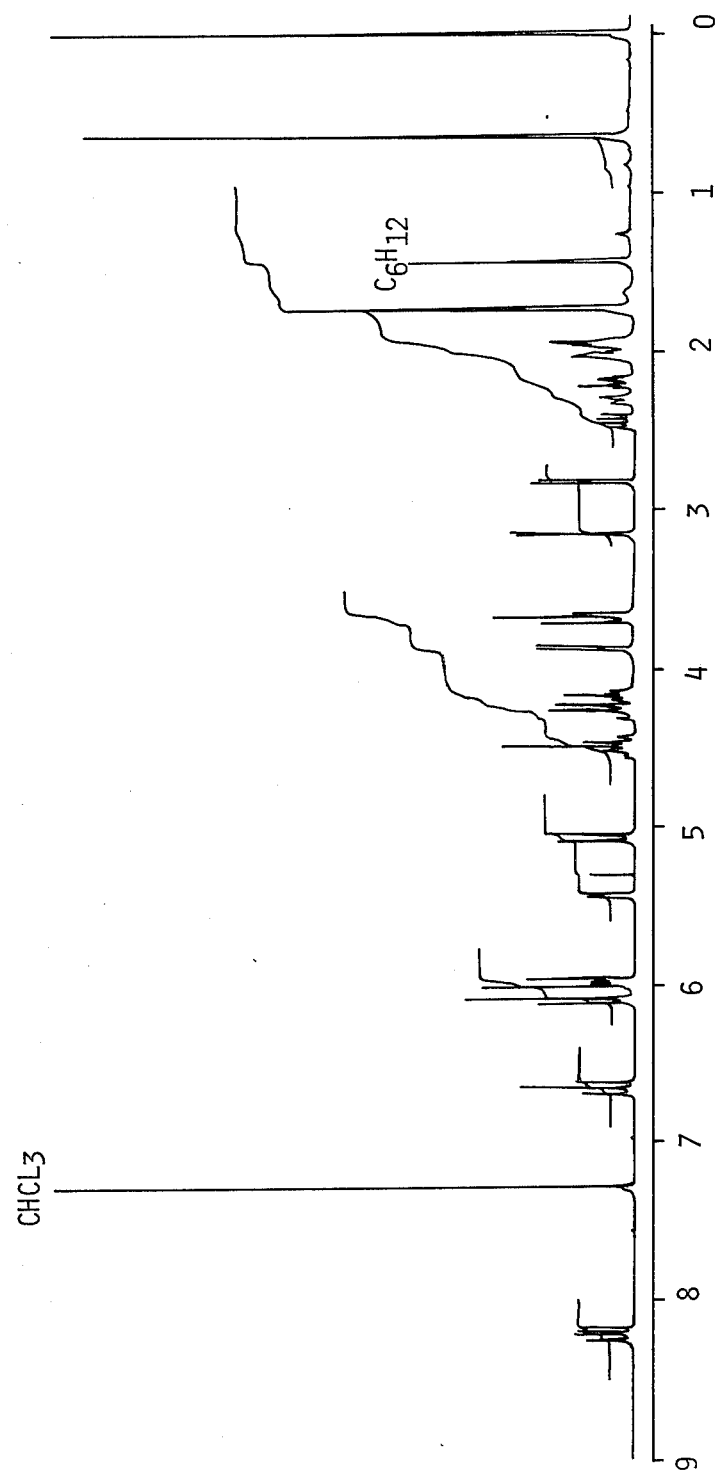
FIG. 5 is the proton magnetic resonance spectrum of 12'-hydroxyverrucarin J in deuterochloroform.
Figure 6:
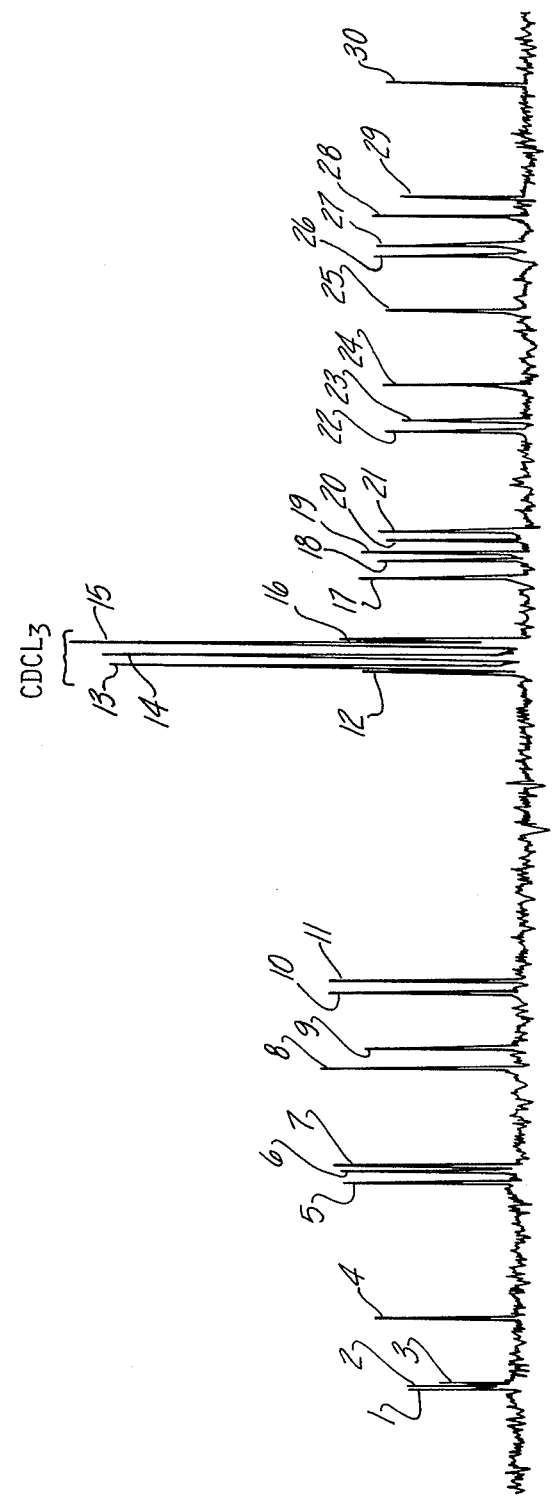
FIG. 6 is the carbon-13 nuclear magnetic resonance spectrum of 12'-hydroxyverrucarin J in deuterochloroform.
Figure 7:
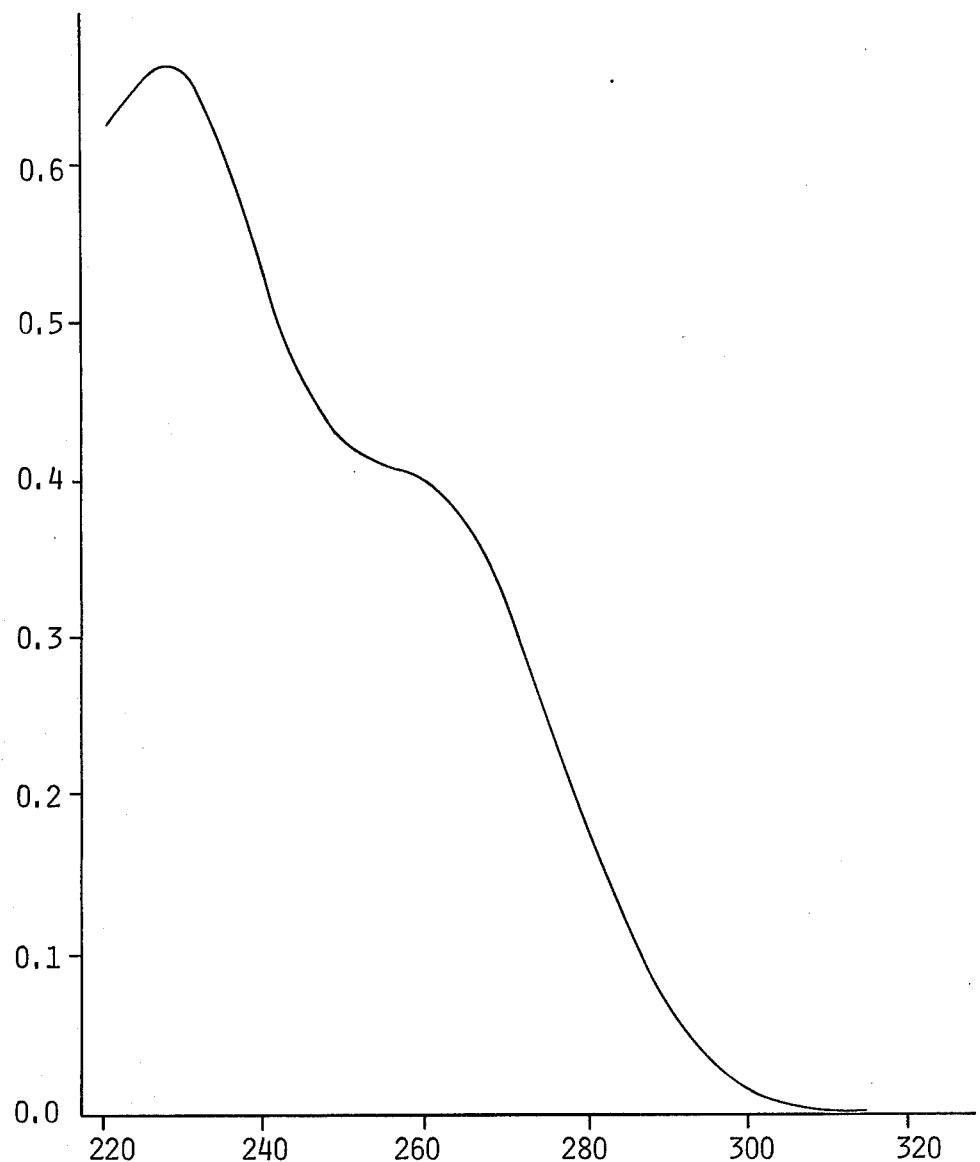
FIG. 7 is the ultraviolet absorption spectrum of iso-satratoxin H in methyl alcohol.
Figure 8:
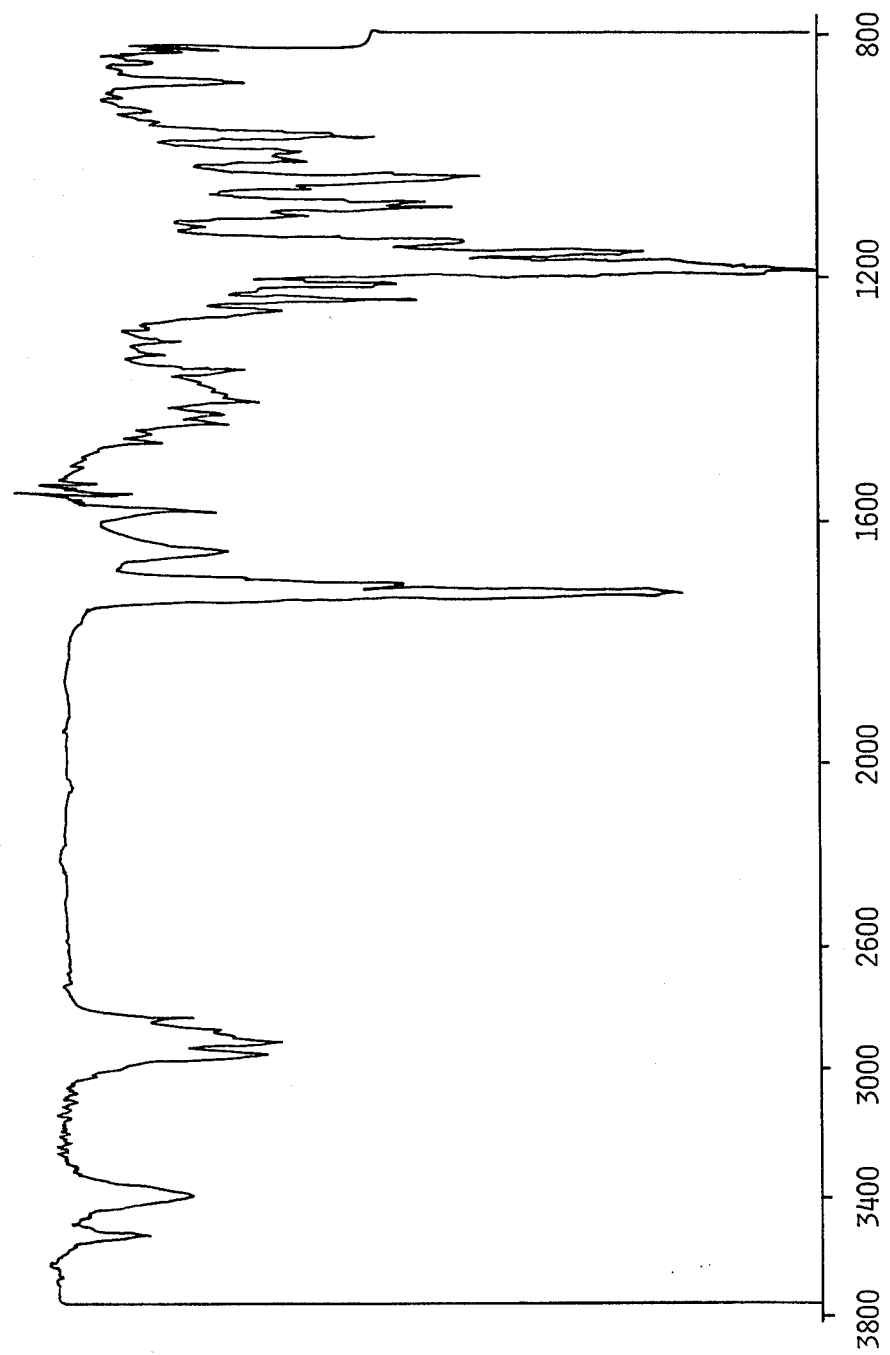
FIG. 8 is the infrared absorption spectrum of iso-satratoxin H in carbon tetrachloride.
Figure 9:
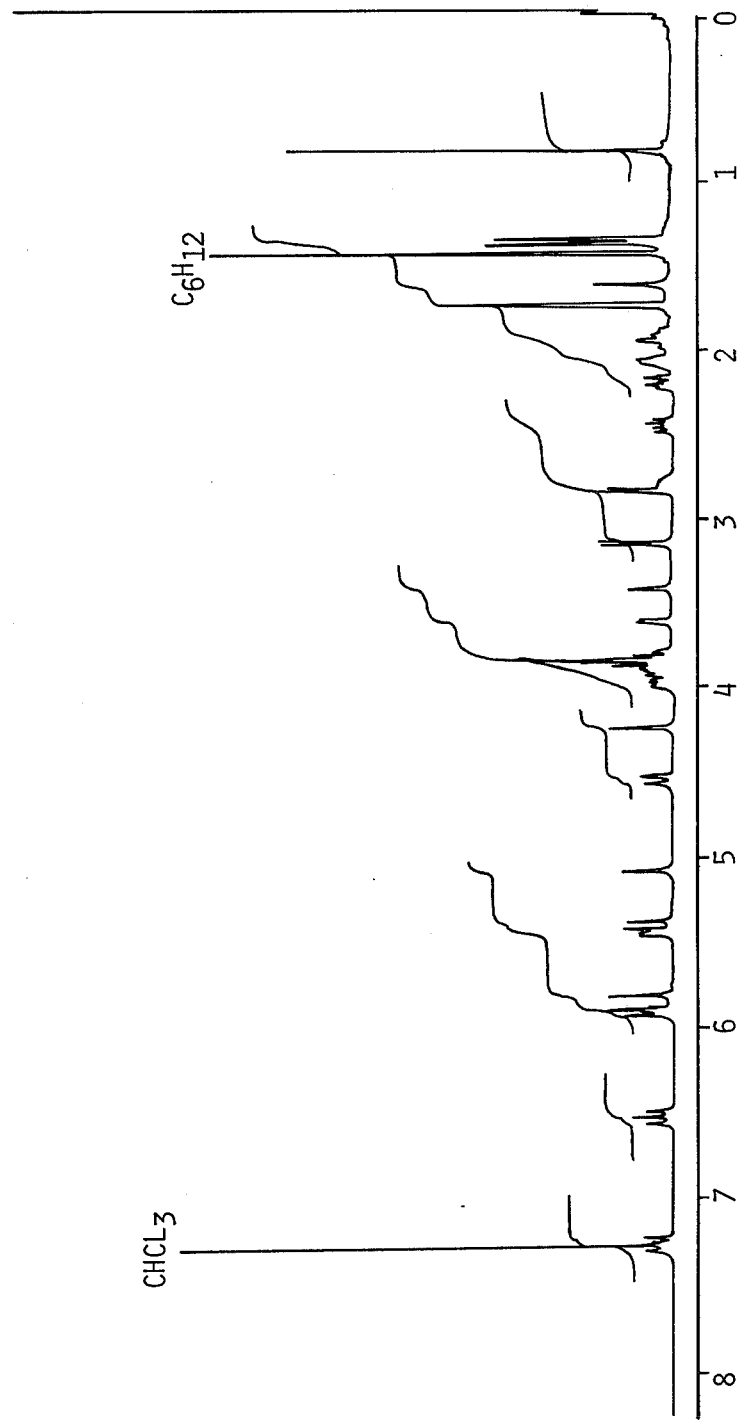
FIG. 9 is the proton magnetic resonance spectrum of iso-satratoxin H in deuterochloroform.

The structural formulae given in FIG. 1 for 12'-hydroxyverrucarin J and in FIG. 2 for iso-satratoxin H are the best representations of the structures of these compounds known to the inventors as of the date of filing of this application. These structures were reached by comparison of the physical and spectral characteristics of 12'-hydroxyverrucarin J and iso-satratoxin H to known closely related prior art compounds. The results obtained from additional physical measurements, such as those obtained for example, from X-ray crystallography may require future modification of the structures depicted in FIGS. 1 and 2. Any such possible future refinement of these structural formulae is intended to be included within the scope of the present invention.

The compounds of the invention may exist in unsolvated as well as solvated forms, including hydrated forms. In general, the solvated forms, with pharmaceutically acceptable solvents such as water, ethanol, and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion of liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient.

The compositions can, if desired, also contain other compatable therapeutic agents.

In therapeutic use as antimicrobial agents, the mammalian dosage range for a 70 kg subject is from 0.01 to 10 mg/kg of body weight per day or preferably 0.1 to 10 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

We claim:

1. The compound iso-satratoxin H, which is characterized by:

A. An ultraviolet absorption spectrum in methanol with the following properties:

| λmax | $a_1^1$ | ε |
   | --- | --- | --- |
   | 226 nm | 362 | 19,100 |
   | 265 inflection | (219) | 11,600 |

B. An infrared absorption spectrum in CCl₄ having principal absorptions at: 3560, 3440, 2975, 2930, 2855, 1730, 1660, 1595, 1195, 1165, 1145, 1090, 1080, and 970 reciprocal centimeters;

C. A proton nuclear magnetic resonance spectrum having principal signals at: (s=singlet, t=triplet, q=quartet, m=multiplet, dd=double doublet, dt=double triplet); 0.83 s; 1.35 d (J=7); 1.43 s (cyclohexane); 1.61s (H₂O); 1.72 s; 1.92 m; 2.18 dt (J=5,15); 2.45 dd (J=8,15); 2.78 m; 2.83 d (J=4); 3.14 d (J=4); 3.39 s; 3.59 d (J=5); 3.9 m; 4.22 s; 4.54 d (J=13); 5.06 s; 5.39 d (J=17); 5.43 d (J=5); 5.80 d (J=3); 5.9 m; 5.93 d (J=12); 6.52 dd (J=10,12); 7.26 dd (J=10,17); 7.27 s (chloroform) parts per million downfield from tetramethylsilane;

D. Carbon-13 Nuclear Resonance Spectrum in CDCl₃ (FIG. 10); Principal signals at:

| | | | |
   | --- | --- | --- | --- |
   | 166.67 | 79.13 | | 61.5 |
   | 166.35 | 78.69 | | 48.97 |
   | 154.91 | 78.42 | | 48.05 |
   | 142.35 | 77.02 | CDCl₃ | 43.36 |
   | 140.40 | 75.62 | | 34.46 |
   | 134.15 | 75.35 | | 27.61 |
   | 133.56 | 74.65 | | 25.45 |
   | 120.98 | 74.16 | | 23.30 |
   | 118.88 | 68.23 | | 20.33 |
   | 118.23 | 65.48 | | 15.80 |
   | 93.10* | 64.02 | | 7.54 Parts per million downfield from tetramethylsilane |

*Instrument noise

2. A pharmaceutical composition which comprises iso-satratoxin H defined in claim 1 in combination with a pharmaceutically acceptable carrier.

3. A method for treating microbial infections in a mammal which comprises administering an antimicrobial effective amount of the composition defined in claim 2 to said mammal.

* * * * *